US008771961B2

(12) United States Patent
Hess et al.

(10) Patent No.: US 8,771,961 B2
(45) Date of Patent: Jul. 8, 2014

(54) MONITORING MYOCARDIAL INFARCTION AND ITS TREATMENT

(75) Inventors: Georg Hess, Mainz (DE); Andrea Horsch, Mannheim (DE); Dietmar Zdunek, Tutzing (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 253 days.

(21) Appl. No.: 12/748,476

(22) Filed: Mar. 29, 2010

(65) Prior Publication Data

US 2011/0213209 A1    Sep. 1, 2011

Related U.S. Application Data

(63) Continuation of application No. PCT/EP2008/063514, filed on Oct. 9, 2008.

(30) Foreign Application Priority Data

Oct. 10, 2007  (EP) .................................... 07118218

(51) Int. Cl.
*G01N 33/68*    (2006.01)
*A61P 9/00*     (2006.01)
(52) U.S. Cl.
USPC .......................................... 435/7.1; 514/16.4
(58) Field of Classification Search
None
See application file for complete search history.

(56) References Cited

U.S. PATENT DOCUMENTS

2005/0239138 A1    10/2005   Hess et al.

FOREIGN PATENT DOCUMENTS

| EP | 1363128 A2 | 11/2003 |
| EP | 1731910 A1 | 12/2006 |
| EP | 1754719 A2 | 2/2007 |
| EP | 1983345 A1 | 10/2008 |
| WO | 99/06445 A1 | 2/1999 |
| WO | 00/70051 A1 | 11/2000 |
| WO | 2005/113585 A3 | 12/2005 |
| WO | 2008/015254 A3 | 2/2008 |

OTHER PUBLICATIONS

Landmesser et al, 2009. Cardiovascular Research. 81, 519-527.*
Lee et al, 2009. MJA. 190(11): 631-636.*
International Search Report issued Mar. 31, 2009 in PCT Application No. PCT/EP2008/063514.
International Preliminary Report on Patentability issued Apr. 13, 2010 in PCT Application No. PCT/EP2008/063514.
Alpert, Joseph S. et al., Myocardial Infarction Redefined—A Concensus Document of the Joint European Society of Cardiology/American College of Cardiology Committee for the Redefinition of Myocardial Infarction, Journal of the American College of Cardiology, Sep. 2000, pp. 959-969, vol. 36, No. 3.
Anderson, p. A. W. et al., Molecular Basis of Human Cardiac Troponin T Isoforms Expressed in the Developing, Adult, and Failing Heart, Circulation Research, 1995, pp. 681-686, vol. 76.
Baek, Seung Joon et al., Cyclooxyenase Inhibitors Regulate the Expression of a TGF-β Superfamily Member That Has Proapoptotic and Antitumorigenic Activities, Molecular Pharmacology, 2001, pp. 901-908, vol. 59.
Bauskin, Asne R. et al., The propeptide of macrophase inhibitory cytokine (MIC-1), a TGF-β superfamily member, acts as a quality control determinant for correctly folded MIC-1, The EMBO Journal, 2000, pp. 2212-2220, vol. 19, No. 10.
Beck-Da-Silva, Luis et al., Brain natriuretic peptide predicts unsuccessful cardioversion in patients with atrial fibrillation and maintenance of sinus rhythm, Canadian Journal of Cardiology, Oct. 2004, pp. 1245-1248, vol. 20, No. 12.
BÖttner, Martina et al., Characterization of the rat, mouse, and human genes of growth/differentiation factor-15/macrophase inhibiting cytokine-1 (GDF-15/MIC-1), Gene, 1999, pp. 105-111, vol. 237.
Chandrashekhar, Y., Multifunctional role of osteopontin in ventricular remodeling, Journal of Laboratory and Clinical Medicine, Jan. 1, 2005, pp. 5-8, vol. 145, No. 1.
Ferrieres, Gaelle et al., Human cardiac troponin I: precise identification of antigenic epitopes and a prediction of secondary structure, Clinical Chemistry, 1998, pp. 487-493, vol. 44, No. 3.
Greenberg, Barry et al., Role of Aldosterone Blockade for Treatment of Heart Failure and Post-Acute Myocardial Infarction, American Journal of Cardiology, May 22, 2006, pp. 34F-40F, vol. 97 Supplement.
Hong, Seo Na et al., Usefulness of Preprocedural N-Terminal Pro-Brain Natriuretic Peptide in Predicting Angiograhic No-Reflow Phenomenon During Stent Implantation in Patients With ST-Segment Elevation Acute Myocardial Infarction, American Journal of Cardiology, 2007, pp. 631-634, vol. 100.
Hromas, Robert et al., PLAB, a novel placental bone morphogenetic protein, Biochimica et Biophysica Acta, 1997, pp. 40-44, vol. 1354.
Kempf, Tibor et al., Circulating Concentrations of Growth-Differentiation Factor 15 in Apparently Healthy Elderly Individuals and Patients with Chronic Heart Failure as Assessed by a New Immunoradiometric Sandwich Assay, Clinical Chemistry, 2007, pp. 284-291, vol. 53, No. 2.
Kohri, Kenjiro et al., Molecular Cloning and Sequencing of cDNA Encoding Urinary Stone Protein, Which is Identical to Osteopontin, Biochemical and Biophysical Research Communications, Apr. 30, 1992, pp. 859-864, vol. 184, No. 2.

(Continued)

*Primary Examiner* — Zachary Howard
(74) *Attorney, Agent, or Firm* — Dinsmore & Shohl, LLP

(57) ABSTRACT

Disclosed is a method of determining which medication is to be applied in a remodeling process of a subject after a myocardial infarction, the method comprising determining an amount of a natriuretic peptide, a cardiac troponin, and an inflammatory marker in a sample from the subject and initiating a remodeling in the subject, wherein the medication to be applied in the remodeling is selected according to the level of the peptides determined. Also disclosed is a method of monitoring the remodeling, wherein further steps include again determining an amount of the natriuretic peptide, the cardiac troponin, and the inflammatory marker in a sample from the subject, calculating the difference between the values from the first and second measurements, and assessing remodeling success from the data obtained.

19 Claims, 10 Drawing Sheets

(56) References Cited

OTHER PUBLICATIONS

Kusuyama, Takanori et al., Angiotension Blockade Inhibits Osteopontin Expression in Non-infarcted Myocardium After Myocardial Infarction, Journal of Pharmacological Sciences, Jul. 2005, pp. 283-289, vol. 98, No. 3.

Lawton, Lee N. et al., Identification of a novel member of the TGF-beta superfamily highly expressed in human placenta, Gene, 1997, pp. 17-26, No. 203.

Mazzali, M. et al., Osteopontin—a molecule for all seasons, Quarterly Journal of Medicine, 2002, pp. 3-13, vol. 95.

Morrish, D. W. et al., Identification by Subtractive Hybridization of a Spectrum of Novel and unexpected Genes Associated with in Vitro Differentiation of Human Cytotrophoblast Cells, Placenta, 1996, pp. 431-441, vol. 17.

Paralkar, Vishwas M. et al., Cloning and Characterization of a Novel Member of the Transforming Growth Factor-βBone Morphogenetic Protein Family, the Journal of Biological Chemistry, May 29, 1998, pp. 13760-13767, vol. 273, No. 22.

Pearson, Thomas A. et al., Markers of Inflammation and Cardiovascular Disease Application to Clinical and Public Health Practice a Statement for Healthcare Professionals From the Centers for Disease Control and Prevention and the American Heart Association, Circulation, 2003, pp. 499-511, vol. 107.

Suezawa, Chisato et al., Time-dependent changes in plasma osteopontin levels in patients with anterior-wall acute myocardial infarction after successful reperfusion: Correlation with left-ventricular volume and function, Journal of Laboratory and Clinical Medicine, Jan. 1, 2005, pp. 33-40, vol. 145, No. 1.

Tsuchida, Keizo and Tanabe, Kazuhiko, Influence of Paroxysmal Atrial Fibrillation Attack on Brain Natriuretic Peptide Secretion, Journal of Cardiology, Jul. 2004, pp. 1-11, vol. 44, No. 1.

Wollert, Kai C. et al., Prognostic Value of Growth-Differentiation Factor-15 in Patients With Non-St-Elevation Acute Coronary Syndrome, Circulation, 2007, pp. 962-971, vol. 115.

Woo, Patricia et al., Characterization of Genomic and Complementary DNA Sequence of Human C-reactive Protein, and Comparison with the Complementary DNA Sequence of Serum Amyloid P Component, The Journal of Biological Chemistry, Oct. 25, 1985, pp. 13384-13388, vol. 260, No. 24.

Yeh, Edward T. H., CRP as a Mediator of Disease, Circulation, 2004, pp. II-11-II-14, vol. 109, Supplement II.

Yokoyama-Kobayashi, Midori et al., Human cDNA Encoding a Novel TGF-β Superfamily Protein Highly Expressed in Placenta, Journal of Biochemistry, 1997, pp. 622-626, vol. 122.

Johnson, Greg A. et al., "Osteopontin: Roles in Implantation and Placentation," Biology of Reproduction, 2003, pp. 1458-1471, vol. 69.

Stawowy, Philipp, et al., "Increased myocardial expression of osteopontin in patients with advanced heart failure," The European Journal of Heart Failure, 2002, pp. 139-146, vol. 4.

* cited by examiner

MONITORING MYOCARDIAL INFARCTION AND ITS TREATMENT

RELATED APPLICATIONS

This application is a continuation of PCT/EP2008/063514 filed Oct. 9, 2008 and claims priority to EP 07118218.2 filed Oct. 10, 2007.

FIELD OF THE INVENTION

The present invention is concerned with methods and devices for medical diagnosis. Specifically, it relates to a method of assessing (diagnosing) which medication is to be applied when remodeling is initiated in a subject after a myocardial infarction. Furthermore, the invention relates to monitoring the progress of remodeling under administration of a given medication. The method is based on determining the level of several peptides from the group natriuretic peptides, osteopontin, GDF-15, CRP and a cardiac troponin, in particular troponin T, in a body liquid of the individual having suffered from a myocardial infarction, and monitoring the level of the respective peptide. A decision about adapting the medication can be based on the data collected. Moreover, the present invention relates to a diagnostic device and a kit for carrying out the aforementioned method.

BACKGROUND

An aim of modern medicine is to provide personalized or individualized treatment regimens. Those are treatment regimens which take into account a patient's individual needs or risks. Personalized or individual treatment regimens shall be even taken into account for emergency measures where it is required to decide on potential treatment regimens within short periods of time. Heart diseases are the leading cause of morbidity and mortality in the Western hemisphere. The said diseases can remain asymptotic for long periods of time. However, they may have severe consequences once an acute cardiovascular event, such as myocardial infarction, as a cause of the cardiovascular disease occurs.

Heart failure is a condition that can result from any structural or functional cardiac disorder that impairs the ability of the heart to fill with or pump a sufficient amount of blood throughout the body. Even with the best therapy, heart failure is associated with an annual mortality of about 10%. Heart failure is a chronic disease; it can, inter alia, occur either following an acute cardiovascular event (like myocardial infarction), or it can occur, e.g., as a consequence of inflammatory or degenerative changes in myocardial tissue. Heart failure patients are classified according to the NYHA system in classes I, II, III and IV. A patient having heart failure will not be able to fully restore his health without receiving a therapeutic treatment.

Myocardial dysfunction is a general term, describing several pathological states of the heart muscle (myocard). A myocardial dysfunction may be a temporary pathological state (caused by, e.g., ischemia, toxic substances, alcohol, . . . ), contrary to heart failure. Myocardial dysfunction may disappear after removing the underlying cause. A symptomless myocardial dysfunction may, however, also develop into heart failure (which has to be treated in a therapy). A myocardial dysfunction may, however, also be a heart failure, a chronic heart failure, even a severe chronic heart failure.

Myocardial dysfunction and heart failure often remain undiagnosed, particularly when the condition is considered "mild." The conventional diagnostic techniques for heart failure are based on the well known vascular volume stress marker NT-proBNP. However, the diagnosis of heart failure under some medical circumstances based on NT-proBNP appears to be incorrect for a significant number of patients but not all (e.g., Beck 2004, Canadian Journal of Cardiology 20: 1245-1248; Tsuchida 2004, Journal of Cardiology, 44:1-11). However, especially patients which suffer from heart failure would urgently need a supportive therapy of heart failure. On the other hand, as a consequence of an incorrect diagnosis of heart failure, many patients will receive a treatment regimen which is insufficient or which may have even adverse side effects.

Patients having heart failure may also develop an acute cardiac disorder, in general an acute coronary syndrome (ACS). ACS covers the states of unstable angina pectoris UAP and acute myocardial infarction MI.

MI is classified as belonging to coronary heart diseases (CHD) and is preceded by other events also classified as belonging to CHD, like unstable angina pectoris UAP. Symptomatic for UAP is chest pain which is relieved by sublingual administration of nitroglycerin. UAP is caused by a partial occlusion of the coronary vessels leading to hypoxemia and myocardial ischemia. In case the occlusion is too severe or total, a myocardial necrosis (which is the pathological state underlying myocardial infarction) results. MI may occur without obvious symptoms, i.e., the subject does not show any discomfort, and the MI is not preceded by stable or unstable angina pectoris.

UAP, however, is a symptomatic event preceding MI. CHD in a subject may also occur symptomless, i.e., the subject may not feel uncomfortable and exhibit any signs of CHD like shortness of breath, chest pain or others known to the person skilled in the art. The subject, however, may be pathological and suffer from a malfunction of his coronary vessels which may result in a MI and/or congestive heart failure CHF, meaning the heart does not have the capacity to perform as required in order to ensure the necessary provision of blood to the subject's body. This may result in severe complications, one example of which is cardiac death.

Patients suffering from symptoms of an acute cardiovascular event (e.g., myocardial infarction) such as chest pain are currently subjected to a cardiac troponin, generally troponin T based diagnosis. To this end, troponin T levels of the patients are determined. If the amount of troponin T in the blood is elevated, i.e., above 0.1 ng/ml, an acute cardiovascular event is assumed and the patent is treated accordingly.

Myocardial infarction MI is defined as being a necrosis of the myocard of various extent and different localization. The therapy of MI aims at re-establishing perfusion, in particular by invasive methods and anti-platelet therapy. Thereafter, a remodeling is initiated, which is accompanied by the administration of various drugs, according to clinical criteria. Amongst these drugs, ACE antagonists, angiotensin receptor antagonists, diuretics of various action modes, Ca antagonists and digitalis can be used.

In the remodeling process, it is state of the art to measure the level of natriuretic peptides, in particular BNP or NT-proBNP. The diagnostic information obtained is, however, limited. Furthermore, an effective monitoring of the therapy in the remodeling is not possible.

The technical problem underlying the present invention can be seen as the provision of means and methods for complying with the aforementioned needs. The technical problem is solved by the embodiments characterized in the claims and herein below.

SUMMARY OF THE INVENTION

Accordingly, the present invention relates to a method of diagnosing which treatment or combination of treatments is to be applied in the remodeling process of a subject after a myocardial infarction, said method comprising
   a) determining the amount of a natriuretic peptide, a cardiac troponin and at least one inflammatory marker, in a sample of said subject;
   b) initiating a remodeling in the subject, wherein the medication to be applied in the remodeling is selected according to the level of the peptides determined in a).

Furthermore, the present invention relates to a method of monitoring the remodeling in a subject after a myocardial infarction, wherein the remodeling is supported by treatment or a combination of treatments, said method comprising carrying out steps a) and b) as cited beforehand; and the further steps of
   c) again determining the amount of a natriuretic peptide, a cardiac troponin and at least one inflammatory marker, in a sample of said subject;
   d) calculating the difference between the values from the first and second measurement;
   e) assessing, from the data obtained in c) and d), if the remodeling is successful.

In a preferred embodiment, the peptides measured in step c) of the method of monitoring are the same as those measured in step a) of the method of diagnosing.

The method may further comprise the optional step f) deciding on adapting the treatment or medication depending on the results obtained in steps a) to e).

Appropriate inflammatory markers which lend themselves for the method of the present invention are known to the person skilled in the art. Preferred markers include osteopontin, GDF-15 and CRP.

The method of the present invention, preferably, is an in vitro method. Moreover, it may comprise steps in addition to those explicitly mentioned above. For example, further steps may relate to sample pre-treatments or evaluation of the results obtained by the method. The method of the present invention may be also used for monitoring, confirmation, and subclassification of a subject. The method may be carried out manually or assisted by automation. Preferably, step (a) and/or (b) and/or (c) and/or (d) and/or (e) and/or (f) may in total or in part be assisted by automation, e.g., by a suitable robotic and sensory equipment for the determination in steps (a) and/or (b) and/or (c) and/or (e) and/or (f) or a computer-implemented comparison in step (d).

In a preferred embodiment of the method of diagnosing which medication is to be applied in the remodeling process of the present invention, the levels of the peptides are measured at a timepoint which lies 1 to 3 days after the acute event has occurred, preferably 1 to 2 days.

In a preferred embodiment of monitoring the remodeling in a subject after a myocardial infarction, wherein the remodeling is supported by medication of the present invention, the levels of the peptides are measured (monitored) during a time period of several months, depending on the pathological state of the patient, and in intervals which also depend on the patient's state. Starting at the date of the first measurement of the peptides, the levels of the peptides should be measured after 2 to 3 days; then after 1, 2, 3 and 4 weeks; then, up to 3 months, in intervals of 2 to 4 weeks. Thereafter, up to 6 months, the level of the peptides should be determined every month, thereafter every 3 to 6 months. In general, it can be said that peptides, the level of which does not show rapid alterations (like GDF-15 or osteopontin), can be determined in larger intervals than peptides, the level of which is subject to more rapid alterations (like troponin T/I, NT-proBNP and CRP).

DETAILED DESCRIPTION OF THE INVENTION

Figure 1:
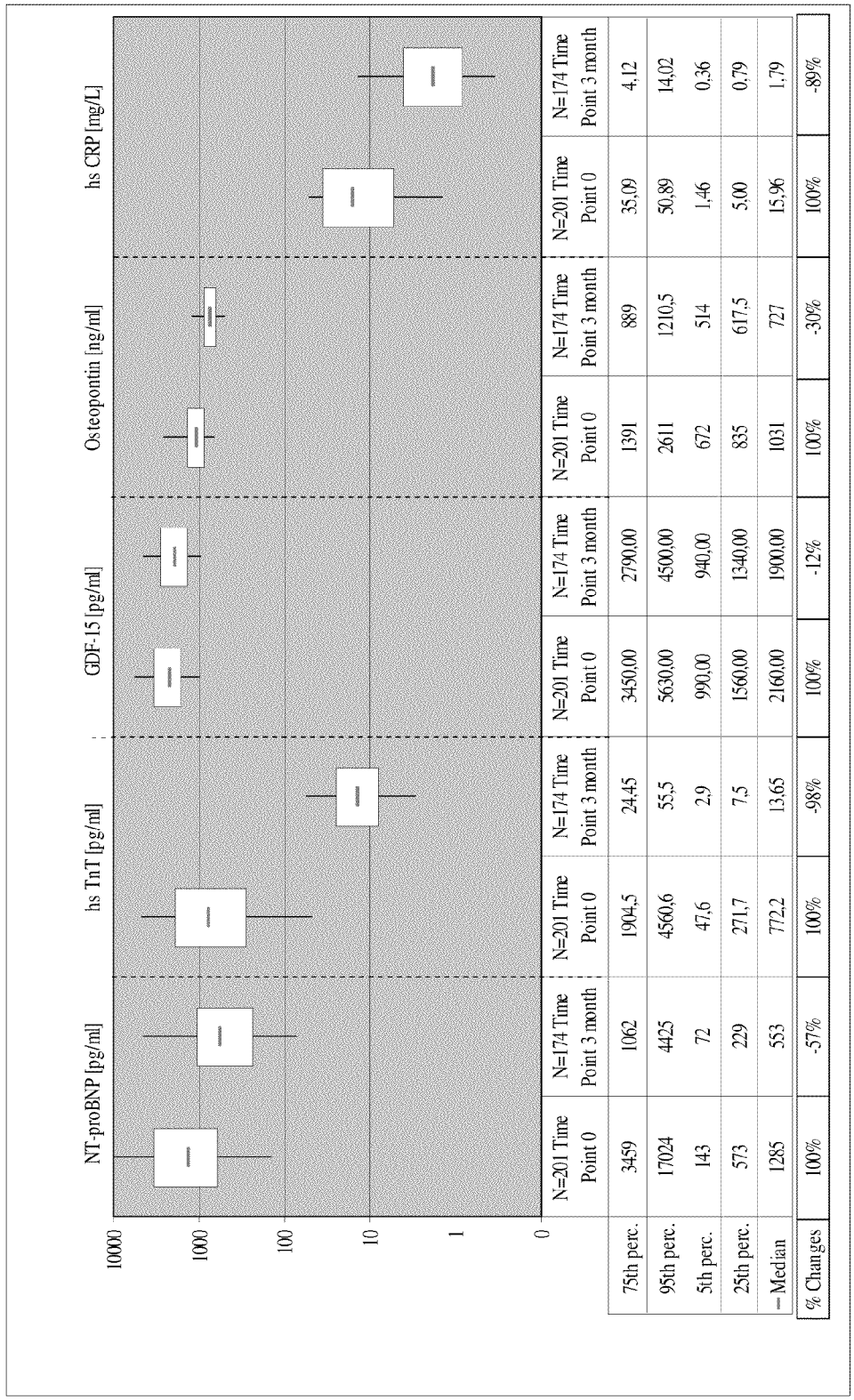
FIG. 1 shows NT-proBNP, hsTNT, GDF-15, ostepontin and hsCRP at time points=0 and =3 month. Values for the median as well as the $5^{th}$, $25^{th}$, $75^{th}$ and $95^{th}$ percentiles as well as the percentage of change are illustrated.

The term "diagnosing" as used herein means assessing as to whether a certain treatment or a combination of treatments should be applied to a subject having suffered from a myocardial infarction MI, in the remodeling process following MI. The treatment may comprise intervention, e.g., surgery, and/or medication, i.e., administration of one or more drugs, or any combination thereof (e.g., more than one intervention or more than one medication or a combination of medication and intervention). The treatment is selected from the following:

A) agents effecting cardiac function, preferably: beta blockers like propranolol, metoprolol, bisoprolol, carvedilol, bucindolol, nebivolol; nitrates; adrenergic agonists, like dobutamine, dopamine, epinephrine, isoprotenerol, norepinephrine, phenylephrine; positive inotropic agents, like digoxin, digitoxin; diuretics, in particular loop diuretics, thiazide and thiazide-like diuretics, K-sparing diuretics, type 1 mineralocorticoid receptor antagonists, carbonic anhydrase inhibitors. vasopressure antagonists.

The information whether these agents should be administered after a MI is given by the level of a natriuretic peptide measured. Suitable natriuretic peptides are BNP, NT-proBNP, ANP, NT-proANP; preferably BNP or NT-proBNP, in particular NT-proBNP.

When a level of natriuretic peptide of, in the case of NT-proBNP, >300 pg/ml, preferably >500 pg/ml, more preferably >800 pg/ml, still more preferably >2000 pg/ml is reached, one or more of the above-cited drugs should be administered.

B) anti-inflammatory drugs, preferably: ACE inhibitors, in particular Enalapril, Captopril, Ramipril, Trandolapril; angiotensin receptor antagonists, in particular Losartan, Valsartan, Irbesartan, Candesartan, Telmisartan, Eprosartan; statines, in particular Atorvastatin, Fluvastatin, Lovastatin, Pravastatin, Rosuvastatin, Simvastatin; NSAIDS; selective COX-2 inhibitors The information whether these agents should be administered after a MI is given by the level of GDF-15 which is indicative for inflammatory processes.

When a level of GDF-15 of >800 pg/ml, preferably >1200 pg/ml, more preferably >1500 pg/ml, in particular >2000 pg/ml is reached, one or more of the above-cited drugs should be administered.

C) anti-inflammatory drugs, preferably: ACE inhibitors, in particular Enalapril, Captopril, Ramipril, Trandolapril; angiotensin receptor antagonists, in particular Losartan, Valsartan, Irbesartan, Candesartan, Telmisartan, Eprosartan; aldosteron antagonists.

The information whether these agents should be administered after a MI is given by the level of osteopontin which is indicative for anti-inflammatory processes.

When a level of osteopontin of >500 pg/ml, preferably >800 pg/ml, more preferably >1200 pg/ml, in particular >1500 pg/ml is reached, one or more of the above-cited drugs should be administered.

D) anti-inflammatory drugs, preferably: statins, in particular Atorvastatin, Fluvastatin, Lovastatin, Pravastatin, Rosuvastatin, Simvastatin The information whether these agents should be administered after a MI is given by the level of CRP which is indicative for anti-inflammatory processes.

When a level of CRP of >3 pg/ml, preferably >5 pg/ml, more preferably >10 pg/ml, in particular >20 pg/ml is reached, one or more of the above-cited drugs should be administered.

E) In general, troponin I and/or T. in particular troponin T, is indicative of an existing myocardial necrosis and the extent of the necrosis; in case no drop in the level of troponin T/I is observed, then this peptide indicates heart failure and/or vascular stenosis which can be treated by percutane coronary intervention.

The information whether these agents should be administered after a MI is given by the level of troponin I and/or troponin T, in particular troponin T which is indicative for heart failure or vascular stenosis.

When the level of troponin T does not drop to values of 80%, preferably 60%, more preferably 20% of the value measured after the acute event, the above-mentioned intervention should be initiated. The intervention should also be initiated in case of a rise of the troponin T/I level.

In the context of the present invention, all peptides cited beforehand may be measured, in order to gain information which allows the best possible assessment of the medication to be applied. This is one embodiment of the present invention. In some cases, however, it may be sufficient to measure, additionally to a natriuretic peptide and a cardiac troponin, two of the mentioned inflammatory markers. Often it is sufficient to measure one inflammatory marker.

In the context of the present invention, only one drug from those cited beforehand can be administered, or two or even more. When more than one drug is administered, the drugs can be selected from one of the groups cited, or from two or more groups.

As will be understood by those skilled in the art, such an assessment is usually not intended to be correct for all (i.e., 100%) of the subjects to be identified. The term, however, requires that a statistically significant portion of subjects can be identified (e.g., a cohort in a cohort study). For example, osteopontin, GDF-15 and CRP overlap in their diagnostic value and may be of a varying value, according to the pathological state of the individual which is to be diagnosed. It can be said that, in the applications according to the present invention, CRP has the lowest specificity, GDF-15 is slow, and osteopontin is fast and most significant when its level changes.

In general, GDF-15 and CRP are the most preferred inflammatory markers of the present invention. As the case may be, and according to the information required, GDF-15 may be preferred over CRP, and vice versa. In the majority of cases, GDF-15 is most preferred for diagnosing which treatment or medication is to be applied, whereas CRP is most preferred, in the majority of cases, for monitoring the remodeling process.

Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. More preferably, at least 60%, at least 70%, at least 80% or at least 90% of the subjects of a population can be properly identified by the method of the present invention.

Diagnosing according to the present invention includes monitoring, confirmation, subclassification and prediction of the relevant disease, symptoms or risks therefor. Confirmation relates to the strengthening or substantiating a diagnosis already performed using other indicators or markers. Subclassification relates to further defining a diagnosis according to different subclasses of the diagnosed disease, e.g., defining according to mild and severe forms of the disease. In particular, it also includes monitoring. Monitoring relates to keeping track of a medication or an already diagnosed disease.

The term "subject" as used herein relates to animals, preferably mammals, and, more preferably, humans. Preferably, the subject referred to in accordance with the aforementioned method suffers from a myocardial infarction or exhibits the symptoms or clinical parameters, such as an increased troponin T level accompanied therewith, i.e., being at least suspect to have suffered from a myocardial infarction.

In accordance with the present invention, determining the amount of the natriuretic peptide or cardiac troponin can be achieved by all known means for determining the amount of a peptide in a sample. Said means comprise immunoassay devices and methods which may utilize labeled molecules in various sandwich, competition, or other assay formats. Said assays will develop a signal which is indicative for the presence or absence of the natriuretic peptide or cardiac troponin.

Moreover, the signal strength can, preferably, be correlated directly or indirectly (e.g., reverse-proportional) to the amount of polypeptide present in a sample. Further suitable methods comprise measuring a physical or chemical property specific for the natriuretic peptide such as its precise molecular mass or NMR spectrum. Said methods comprise, preferably, biosensors, optical devices coupled to immunoassays, biochips, analytical devices such as mass-spectrometers, NMR-analyzers, or chromatography devices. Further, methods include micro-plate ELISA-based methods, fully-automated or robotic immunoassays (available for example on ELECSYS analyzers, Roche Diagnostics GmbH), CBA (an enzymatic cobalt binding assay, available for example on Roche-Hitachi analyzers), and latex agglutination assays (available for example on Roche-Hitachi analyzers). The methods and means for measurement also include Point-of-care devices, such as the Cardiac Reader (available from Roche Diagnostics).

Point-of-care devices are generally understood as devices which enable measuring at the patient bedside. An example is the Cardiac Reader (available from Roche Diagnostics), in combination, e.g., with test strips for NT-proBNP (available as "Cardiac proBNP" from Roche Diagnostics). Such test may employ two (preferably monoclonal) antibodies directed against the peptide of interest (e.g., a BNP-type peptide). The antibodies can be identical to the antibodies used, e.g., in the ELECSYS or Cobas assays. E.g., the first antibody is labeled with biotin while the second antibody is labeled with gold particles. The test can be started by adding a small amount (e.g., 150 µl) of blood sample onto the test strip (e.g., into a sample well of the test strip). The erythrocytes in the sample may be separated from the remaining plasma before or after addition to the test strip, e.g., if the sample flows through a suitable fleece (e.g., a glass fiber fleece). Said separating means (e.g., fleece) is preferably part of the test strip. The antibodies (preferably already present on the test strip) are dissolved in the remaining plasma. The antibodies are capable of binding to the peptide or polypeptide of interest, forming a three-membered sandwich complex. The antibodies (bound or unbound) flow through the strip into a detection zone. The detection zone comprises means for detecting the bound complex, e.g., it may comprise streptavidin. This immobilizes the complexes and visualizes the immobilized complex as a purple line by the gold-labeled antibody. Preferably, remaining free gold-labeled antibody may then move further down the strip where it is captured in a zone comprising a synthetic peptide or polypeptide comprising the epitope of the BNP-type peptide to be detected, visualized as a separate purple line. The presence of such second line can serve as a control because it indicates that the sample flow as worked correctly and the antibody is intact. the test strip may comprise a label indicating which peptide or polypeptide of interest can be detected with the strip. It may also comprise a barcode or other code readable by a device for optical measurement of the amount of label detectable in the detection zone. Such barcode may include information indicating which peptide or polypeptide of interest can be detected with the strip. The barcode may also include lot-specific information about the test strip.

The term "cardiac troponin" refers to all troponin isoforms expressed in cells of the heart and, preferably, the subendocardial cells. These isoforms are well characterized in the art as described, e.g., in Anderson 1995, Circulation Research, vol. 76, no. 4: 681-686 and Ferrieres 1998, Clinical Chemistry, 44: 487-493.

Preferably, cardiac troponin refers to troponin T and/or troponin I.

Accordingly, both troponins may be determined in the method of the present invention together, i.e., simultaneously or sequentially, or individually, i.e., without determining the other isoform at all.

Amino acid sequences for human troponin T and human troponin I are disclosed in Anderson, loc cit and Ferrieres 1998, Clinical Chemistry, 44: 487-493. The term "cardiac troponin" encompasses also variants of the aforementioned specific troponins, i.e., preferably, of troponin T or troponin I. Such variants have at least the same essential biological and immunological properties as the specific cardiac troponins. In particular, they share the same essential biological and immunological properties if they are detectable by the same specific assays referred to in this specification, e.g., by ELISA Assays using polyclonal or monoclonal antibodies specifically recognizing the said cardiac troponins. Moreover, it is to be understood that a variant as referred to in accordance with the present invention shall have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino acid sequence of the specific troponin. Variants may be allelic variants or any other species specific homologs, paralogs, or orthologs. Moreover, the variants referred to herein include fragments of the specific cardiac troponins or the aforementioned types of variants as long as these fragments have the essential immunological and biological properties as referred to above. Such fragments may be, e.g., degradation products of the troponins. Further included are variants which differ due to posttranslational modifications such as phosphorylation or myristylation. A particularly preferred troponin T assay in the context of the present invention is the ELECSYS 2010 analyzer (Roche Diagnostics) with a detection limit of 0.001 ng/ml.

If the amount of troponin T in the blood is elevated, i.e., above 0.1 ng/ml, an acute cardiovascular event is assumed and the patent is treated accordingly.

The term "growth-differentiation factor-15" or "GDF-15" relates to a polypeptide being a member of the transforming growth factor (TGF)-β cytokine superfamily. The terms polypeptide, peptide and protein are used interchangeable throughout this specification. GDF-15 was originally cloned as macrophage-inhibitory cytokine-1 and later also identified as placental transforming growth factor-β, placental bone morphogenetic protein, non-steroidal anti-inflammatory drug-activated gene-1, and prostate-derived factor (Bootcov loc cit; Hromas, 1997 Biochim Biophys Acta 1354:40-44; Lawton 1997, Gene 203:17-26; Yokoyama-Kobayashi 1997, J Biochem (Tokyo), 122:622-626; Paralkar 1998, J Biol Chem 273:13760-13767). Similar to other TGF-(3-related cytokines, GDF-15 is synthesized as an inactive precursor protein, which undergoes disulfide-linked homodimerization. Upon proteolytic cleavage of the N-terminal pro-peptide, GDF-15 is secreted as a ~28 kDa dimeric protein (Bauskin 2000, Embo J 19:2212-2220). Amino acid sequences for GDF-15 are disclosed in WO99/06445, WO00/70051, WO2005/113585, Bottner 1999, Gene 237: 105-111, Bootcov loc. cit, Tan loc. cit., Baek 2001, Mol Pharmacol 59: 901-908, Hromas loc cit, Paralkar loc cit, Morrish 1996, Placenta 17:431-441 or Yokoyama-Kobayashi loc cit. GDF-15 as used herein encompasses also variants of the aforementioned specific GDF-15 polypeptides. Such variants have at least the same essential biological and immunological properties as the specific GDF-15 polypeptides. In particular, they share the same essential biological and immunological properties if they are detectable by the same specific assays referred to in this specification, e.g., by ELISA assays using polyclonal or monoclonal antibodies specifically recognizing the said GDF-15 polypeptides. Moreover, it is to be understood that a variant as referred to in accordance with the present invention shall have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino sequence of the specific GDF-15 polypeptides. Moreover, the variants referred to herein include fragments of the specific GDF-15 polypeptides or the aforementioned types of variants as long as these fragments have the essential immunological and biological properties as referred to above. Such fragments may be, e.g., degradation products of the GDF-15 polypeptides. Further included are variants which differ due to posttranslational modifications such as phosphorylation or myristylation. A preferred GDF-15 assay in the context of the present invention is the assay as described by Wollert et al. in Clinical Chemistry 53, No 2, 2007, p. 284-291.

Osteopontin, herein also referred to as OPN, is a negatively-charged acidic hydrophilic polypeptide. The terms polypeptide, peptide and protein are used interchangeable throughout this specification. Osteopontin is a multifunctional protein and is secreted into all body fluids. Although highly expressed in bone, it is also expressed by various cell types including macrophages, endothelial cells, smooth muscle cells and epithelial cells. Moreover, it was disclosed that expression of OPN is increased in the myocardium of patients with advance heart failure. OPN is an acidic member of the small integrin-binding ligand N-linked glycoprotein (SIBLING) family of proteins that include bone sialoprotein, dentin matrix protein I, dentin sialophosphoprotein, and matrix extracellular phosphoglycoprotein, which are the products of five genes clustered along human chromosome 4. There is evidence of alternative splicing, although the functional significance of this still needs to be elucidated. In general, OPN is a monomer ranging in length from 264 to 301 amino acids that undergoes extensive posttranslational modification, including phosphorylation, glycosylation, and cleavage, resulting in molecular mass variants ranging from 25 to 75 kDa. Genes encoding OPN have been cloned, e.g., from rat, mouse, human, cow, chicken, rabbit, and sheep (Stawowy et al., loc cit.; Mazzali et al., Osteopontin—A molecule for all season. QJM 95(1):3-13; Johnson et al. 2003, Osteopontin: roles in implantation and placentation. Kohri et al. (1992) Biochem Biophys Res Commun 1992 184(2):859-64). An antibody against an isoform of Osteopontin is disclosed, e.g., in EP 1 754 719. Osteopontin as used herein encompasses also variants of Osteopontin polypeptides. Such variants have at least the same essential biological and immunological properties as the specific Osteopontin polypeptides. In particular, they share the same essential biological and immunological properties if they are detectable by the same specific assays referred to in this specification, e.g., by ELISA assays using polyclonal or monoclonal antibodies specifically recognizing the said Osteopontin polypeptides. A preferred assay is described in the accompanying Examples. Moreover, it is to be understood that a variant as referred to in accordance with the present invention shall have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino sequence of the specific Osteopontin polypeptides. Moreover, the variants referred to herein include fragments of the specific Osteopontin polypeptides or the aforementioned types of variants as long as these fragments have the essential immunological and biological properties as referred to above. Such fragments may be, e.g., degradation products of the Osteopontin polypeptides. Further included are variants which differ due to posttranslational modifications such as phosphorylation or myristylation. A preferred osteopontin assay in the context of the present invention is the Human Osteopontin Assay Kit of IBL (Immuno-Biological Laboratories Co, Ltd, 5-1 Aramachi, Takasaki-shi, Gunma, 370-0831, Japan), also available at IBL Gesellschaft für Immunochemie and Immunbiologie mbH, Flughafenstr. 52a, D-22335 Hamburg.

CRP, herein also referred to as C-reactive protein, is an acute phase protein that was discovered more than 75 years ago to be a blood protein that binds to the C-polysaccharide of pneumococci. CRP consists of five single subunits, which are non covalently linked and assembled as a cyclic pentamer with a molecular weight of approximately 110-140 kDa. Preferably, CRP as used herein relates to human CRP. The sequence of human CRP is well known and disclosed, e.g., by Woo et al. (J. Biol. Chem. 1985. 260 (24), 13384-13388). The level of CRP is usually low in normal individuals but can rise 100- to 200-fold or higher due to inflammation, infection or injury (Yeh (2004) Circulation. 2004; 109:II-11-II-14). It is known that CRP is an independent factor for the prediction of a cardiovascular risk. Particularly, it has been shown that CRP is suitable as a predictor for myocardial infarction, stroke, peripheral arterial disease and sudden cardiac death. Moreover, elevated CRP amounts may also predict recurrent ischemia and death in subjects with acute coronary syndrome (ACS) and those undergoing coronary intervention. Determination of CRP is recommended by expert panels (e.g., by the American Heart Association) in patients with a risk of coronary heart disease (see also Pearson et al. (2003) Markers of Inflammation and Cardiovascular Disease. Circulation, 107: 499-511).

Preferably, the amount of CRP in a sample of a subject is determined by using CRP assays with a high sensitivity. The CRP determined by such assays is frequently also referred to as high sensitivity CRP (hsCRP). hsCRP assays are nowadays used to predict the risk of heart disease. Suitable hsCRP assays are known in the art. A particularly preferred hsCRP assay in the context of the present invention is the Roche/Hitachi CRP (Latex) HS test with a detection limit of 0.1 mg/l.

In the context of the present invention, the term "remodeling" refers to angiogenic processes by which the necrotic areas and connective tissue are replaced and its function is re-established by non concentric hypertrophy.

In order to establish a diagnosis as laid out beforehand, the present invention teaches to measure the level of peptides other than a natriuretic peptide, in order to establish a diagnosis. Furthermore, the present invention can be used to monitor the remodeling process in an individual after MI and, as the case may be, decide on continuing, modifying or terminating the administration of the medicament.

Individuals having only a minor myocardial dysfunction prior to MI (ACS), or having no myocardial dysfunction at all, redevelop myocardial functionality to at least a high extent after several weeks or months, e.g., 3 months, by remodeling. In contrast, individuals having only a preexisting considerable myocardial dysfunction (prior to MI (ACS)) hardly redevelop myocardial functionality after several weeks or months. In these cases, a therapy can be initiated immediately after MI (ACS) has occurred, which is accompanied by the administration of certain drugs, as laid out beforehand. The therapy can be monitored by measuring the level of troponin T or I, osteopontin, CRP and/or GDF-15.

In many cases, it is not appropriate to cite values of the respective peptide upon which a decision about continuing, modifying or terminating the medication can be based. For CRP, it can be said that a level of about 33 pg/ml should be reached before the medical treatment is terminated. In case of NT-proBNP, the drop in the level of the peptide depends on the degree of heart failure. The drop in the level of troponin T/I depends on the degree of heart failure and coronary stenosis. For GDF-15, a drop of ≥20% generally indicates that the amount of administered drug can be lowered. For osteopontin, a drop of ≥40% generally indicates that the amount of administered drug can be lowered.

The method according to the present invention comprises determining the amount of NT-proBNP in a sample of said subject, and determining the amount of one of the peptides cited above in a sample of the subject. These steps may be carried out simultaneously, or prior or subsequently.

As discussed above already, a preferred reference amount serving as a threshold may be derived from the ULN. The ULN for a given population of subjects can be determined as specified elsewhere in this description.

The present invention in relates to cardiac disorders, preferably from the group myocardial dysfunction and heart failure.

The term "myocardial dysfunction" as used herein is a general term and relates to several pathological states of the myocard. A myocardial dysfunction may be a temporary pathological state (caused by, e.g., ischemia, toxic substances, alcohol, . . . ). Myocardial dysfunction may disappear after removing the underlying cause. In the context of the present invention, the myocardial dysfunction can be a symptomless myocardial dysfunction. A myocardial dysfunction, in particular a symptomless myocardial dysfunction, may also develop into heart failure. A myocardial dysfunction may also be a severe chronic heart failure. In general, a myocardial dysfunction is an impaired systolic and/or diastolic function of the heart, and a myocardial dysfunction may occur with or without heart failure. Any heart failure mentioned beforehand my be symptomless.

The term "heart failure" as used herein relates to an impaired systolic and/or diastolic function of the heart. Preferably, heart failure referred to herein is also chronic heart failure. Heart failure can be classified into a functional classification system according to the New York Heart Association (NYHA). Patients of NYHA Class I have no obvious symptoms of cardiovascular disease but already have objective evidence of functional impairment. Physical activity is not limited, and ordinary physical activity does not cause undue fatigue, palpitation, or dyspnea (shortness of breath). Patients of NYHA class II have slight limitation of physical activity. They are comfortable at rest, but ordinary physical activity results in fatigue, palpitation, or dyspnea. Patients of NYHA class III show a marked limitation of physical activity. They are comfortable at rest, but less than ordinary activity causes fatigue, palpitation, or dyspnea. Patients of NYHA class IV are unable to carry out any physical activity without discomfort. They show symptoms of cardiac insufficiency at rest. Heart failure, i.e., an impaired systolic and/or diastolic function of the heart, can be determined also by, for example, echocardiography, angiography, scintigraphy, or magnetic resonance imaging. This functional impairment can be accompanied by symptoms of heart failure as outlined above (NYHA class II-IV), although some patients may present without significant symptoms (NYHA I). Moreover, heart failure is also apparent by a reduced left ventricular ejection fraction (LVEF). More preferably, heart failure as used herein is accompanied by a left ventricular ejection fraction (LVEF) of less than 60%, of 40% to 60% or less than 40%.

The term "acute cardiovascular event" refers to all events which suddenly appear, i.e., without previous clinical signs or symptoms, and which severely affect the diastolic or systolic blood flow rate. Histopathologically, the acute cardiovascular event referred to herein shall be accompanied by a sudden ischemia of heart muscle cells accompanied by severe necrosis of said cells. Preferably, the subject suffering from an acute cardiovascular event will also suffer from typical symptoms such as chest, epigastric, arm, wrist or jaw discomfort or pain whereby, in particular, the chest pain may radiate to the arm, back or shoulder. Further symptoms of an acute cardiovascular event may be unexplained nausea or vomiting, persistent shortness of breath, weakness, dizziness, lightheadedness or syncope as well as any combinations thereof. Preferably, the acute cardiovascular event referred to herein is an acute coronary syndrome (ACS), i.e., either an unstable angina pectoris (UAP) or myocardial infarction (MI). Most preferably, the acute cardiovascular event is MI including ST-elevated MI and non-ST-elevated MI. Moreover, the cardiovascular event also encompasses stroke. The occurring of an MI can be followed by a left ventricular dysfunction (LVD). Finally, LVD patients undergo congestive heart failure (CHF) with a considerable mortality rate. Further details on the definitions, symptoms and clinical signs such as electrocardiographic signs, are found in Joint European Society of Cardiology/American Society of Cardiology, 2000, J American College of Cardiology, Vol. 36, No. 3: 959-969.

The term "sample" refers to a sample of a body fluid, to a sample of separated cells or to a sample from a tissue or an organ. Samples of body fluids can be obtained by well known techniques and include, preferably, samples of blood, plasma, serum, or urine, more preferably, samples of blood, plasma or serum. Tissue or organ samples may be obtained from any tissue or organ by, e.g., biopsy. Separated cells may be obtained from the body fluids or the tissues or organs by separating techniques such as centrifugation or cell sorting. Preferably, cell-, tissue- or organ samples are obtained from those cells, tissues or organs which express or produce the peptides referred to herein.

Determining the amount of the peptides or polypeptides referred to in this specification relates to measuring the amount or concentration, preferably semi-quantitatively or quantitatively. Measuring can be done directly or indirectly. Direct measuring relates to measuring the amount or concentration of the peptide or polypeptide based on a signal which is obtained from the peptide or polypeptide itself and the intensity of which directly correlates with the number of molecules of the peptide present in the sample. Such a signal—sometimes referred to herein as intensity signal—may be obtained, e.g., by measuring an intensity value of a specific physical or chemical property of the peptide or polypeptide. Indirect measuring includes measuring of a signal obtained from a secondary component (i.e., a component not being the peptide or polypeptide itself) or a biological read out system, e.g., measurable cellular responses, ligands, labels, or enzymatic reaction products.

In accordance with the present invention, determining the amount of a peptide or polypeptide can be achieved by all known means for determining the amount of a peptide in a sample. Said means comprise immunoassay devices and methods which may utilize labeled molecules in various sandwich, competition, or other assay formats. Said assays will develop a signal which is indicative for the presence or absence of the peptide or polypeptide. Moreover, the signal strength can, preferably, be correlated directly or indirectly (e.g., reverse-proportional) to the amount of polypeptide present in a sample. Further suitable methods comprise measuring a physical or chemical property specific for the peptide or polypeptide such as its precise molecular mass or NMR spectrum. Said methods comprise, preferably, biosensors, optical devices coupled to immunoassays, biochips, analytical devices such as mass-spectrometers, NMR-analyzers, or chromatography devices. Further, methods include microplate ELISA-based methods, fully-automated or robotic immunoassays (available for example on ELECSYS analyzers), CBA (an enzymatic cobalt binding assay, available for example on Roche-Hitachi analyzers), and latex agglutination assays (available for example on Roche-Hitachi analyzers).

Preferably, determining the amount of a peptide or polypeptide comprises the steps of (a) contacting a cell capable of eliciting a cellular response the intensity of which is indicative of the amount of the peptide or polypeptide with the said peptide or polypeptide for an adequate period of time, (b) measuring the cellular response. For measuring cellular responses, the sample or processed sample is, preferably, added to a cell culture and an internal or external cellular response is measured. The cellular response may include the measurable expression of a reporter gene or the secretion of a substance, e.g., a peptide, polypeptide, or a small molecule. The expression or substance shall generate an intensity signal which correlates to the amount of the peptide or polypeptide.

Also preferably, determining the amount of a peptide or polypeptide comprises the step of measuring a specific intensity signal obtainable from the peptide or polypeptide in the sample. As described above, such a signal may be the signal intensity observed at an m/z variable specific for the peptide or polypeptide observed in mass spectra or a NMR spectrum specific for the peptide or polypeptide.

Determining the amount of a peptide or polypeptide may, preferably, comprise the steps of (a) contacting the peptide with a specific ligand, (b) (optionally) removing non-bound ligand, (c) measuring the amount of bound ligand. The bound ligand will generate an intensity signal. Binding according to the present invention includes both covalent and non-covalent binding. A ligand according to the present invention can be any compound, e.g., a peptide, polypeptide, nucleic acid, or small molecule, binding to the peptide or polypeptide described herein. Preferred ligands include antibodies, nucleic acids, peptides or polypeptides such as receptors or binding partners for the peptide or polypeptide and fragments thereof comprising the binding domains for the peptides, and aptamers, e.g., nucleic acid or peptide aptamers. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g., phage display. Antibodies as referred to herein include both polyclonal and monoclonal antibodies, as well as fragments thereof, such as Fv, Fab and F(ab)2 fragments that are capable of binding antigen or hapten. The present invention also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the ligand or agent binds specifically to the peptide or polypeptide. Specific binding according to the present invention means that the ligand or agent should not bind substantially to ("cross-react" with) another peptide, polypeptide or substance present in the sample to be analyzed. Preferably, the specifically bound peptide or polypeptide should be bound with at least 3 times higher, more preferably at least 10 times higher and even more preferably at least 50 times higher affinity than any other relevant peptide or polypeptide. Non-specific binding may be tolerable, if it can still be distinguished and measured unequivocally, e.g., according to its size on a Western Blot, or by its relatively higher abundance in the sample. Binding of the ligand can be measured by any method known in the art. Preferably, said method is semi-quantitative or quantitative. Suitable methods are described in the following.

First, binding of a ligand may be measured directly, e.g., by NMR or surface plasmon resonance.

Second, if the ligand also serves as a substrate of an enzymatic activity of the peptide or polypeptide of interest, an enzymatic reaction product may be measured (e.g., the amount of a protease can be measured by measuring the amount of cleaved substrate, e.g., on a Western Blot). Alternatively, the ligand may exhibit enzymatic properties itself and the "ligand/peptide or polypeptide" complex or the ligand which was bound by the peptide or polypeptide, respectively, may be contacted with a suitable substrate allowing detection by the generation of an intensity signal. For measurement of enzymatic reaction products, preferably the amount of substrate is saturating. The substrate may also be labeled with a detectable label prior to the reaction. Preferably, the sample is contacted with the substrate for an adequate period of time. An adequate period of time refers to the time necessary for an detectable, preferably measurable, amount of product to be produced. Instead of measuring the amount of product, the time necessary for appearance of a given (e.g., detectable) amount of product can be measured.

Third, the ligand may be coupled covalently or non-covalently to a label allowing detection and measurement of the ligand. Labeling may be done by direct or indirect methods. Direct labeling involves coupling of the label directly (covalently or non-covalently) to the ligand. Indirect labeling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.). The ligand or substrate may also be "tagged" with one or more tags as known in the art. Such tags may then be targets for higher order ligands. Suitable tags include biotin, digoxigenin, His-Tag, Glutathione-S-Transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g., magnetic beads", including paramagnetic and superparamagnetic labels), and fluorescent labels.

Enzymatically active labels include, e.g., horseradish peroxidase, alkaline phosphatase, beta-Galactosidase, Luciferase, and derivatives thereof. Suitable substrates for detection include di-amino-benzidine (DAB), 3,3'-5,5'-tetramethyl-benzidine, NBT-BCIP (4-nitro blue tetrazolium chloride and 5-bromo-4-chloro-3-indolyl-phosphate, available as ready-made stock solution from Roche Diagnostics), CDP-Star (Amersham Biosciences), ECF (Amersham Biosciences). A suitable enzyme-substrate combination may result in a colored reaction product, fluorescence or chemiluminescence, which can be measured according to methods known in the art (e.g., using a light-sensitive film or a suitable camera system). As for measuring the enzymatic reaction, the criteria given above apply analogously. Typical fluorescent labels include fluorescent proteins (such as GFP and its derivatives), Cy3, Cy5, Texas Red, Fluorescein, and the Alexa dyes (e.g., Alexa 568). Further fluorescent labels are available, e.g., from Molecular Probes (Oregon). Also the use of quantum dots as fluorescent labels is contemplated. Typical radioactive labels include 35S, 125I, 32P, 33P and the like. A radioactive label can be detected by any method known and appropriate, e.g., a light-sensitive film or a phosphor imager. Suitable measurement methods according the present invention also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immunoassay (DELFIA), scintillation proximity assay (SPA), turbidimetry, nephelometry, latex-enhanced turbidimetry or nephelometry, or solid phase immune tests. Further methods known in the art (such as gel electrophoresis, 2D gel electrophoresis, SDS polyacrylamide gel electrophoresis (SDS-PAGE), Western Blotting, and mass spectrometry), can be used alone or in combination with labeling or other detection methods as described above.

The amount of a peptide or polypeptide may be, also preferably, determined as follows: (a) contacting a solid support comprising a ligand for the peptide or polypeptide as specified above with a sample comprising the peptide or polypeptide and (b) measuring the amount peptide or polypeptide which is bound to the support. The ligand, preferably chosen from the group consisting of nucleic acids, peptides, polypeptides, antibodies and aptamers, is preferably present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said ligand are well known and include, but are not limited to ionic, hydrophobic, covalent interactions and the like. It is also contemplated to use "suspension arrays" as arrays according to the present invention (Nolan 2002, Trends Biotechnol. 20(1):9-12). In such suspension arrays, the carrier, e.g., a microbead or microsphere, is present in suspension. The array consists of different microbeads or microspheres, possibly labeled, carrying different ligands. Methods of producing such arrays, for example based on solid-phase chemistry and photo-labile protective groups, are generally known (U.S. Pat. No. 5,744,305).

The term "amount" as used herein encompasses the absolute amount of a polypeptide or peptide, the relative amount or concentration of the said polypeptide or peptide as well as any value or parameter which correlates thereto or can be derived therefrom. Such values or parameters comprise intensity signal values from all specific physical or chemical properties obtained from the said peptides by direct measurements, e.g., intensity values in mass spectra or NMR spectra. Moreover, encompassed are all values or parameters which are obtained by indirect measurements specified elsewhere in this description, e.g., response levels determined from biological read out systems in response to the peptides or intensity signals obtained from specifically bound ligands. It is to be understood that values correlating to the aforementioned amounts or parameters can also be obtained by all standard mathematical operations.

Based on the method of the present invention, myocardial dysfunction, in particular heart failure existing prior to an ACS, in particular a MI (and still existing after the acute event) can be diagnosed and treated more efficiently. The method of the present invention, advantageously, allows for a reliable, fast and less cost intensive diagnosis and can be implemented even in portable assays, such as test stripes. Therefore, the method is particularly well suited for diagnosing emergency patients. Thanks to the findings of the present invention, a suitable therapy for a subject can be timely and reliably selected, e.g., a therapy for heart failure. Severe side effects caused by the late and/or wrong treatment of patients can be avoided.

The present invention, furthermore, relates to a device of diagnosing which treatment or combination of treatments is to be applied in the remodeling process of a subject after a myocardial infarction, said device comprising
  a) means for determining the amount of a natriuretic peptide and the amount of a cardiac troponin, in a sample of said subject,
  b) means for determining the amount of an inflammatory marker, preferably osteopontin, GDF-15, and/or CRP, in a sample of said subject; optionally
  c) means for diagnosing if a remodeling in the subject is to be initiated, wherein the medication to be applied in the remodeling is selected according to the level of the peptides determined in a) and b).

The present invention also relates to a device of monitoring the remodeling in a subject after a myocardial infarction, wherein the remodeling is supported by treatment or a combination of treatments, said device comprising
  d) means for again determining the amount of a natriuretic peptide and the amount of a cardiac troponin, in a sample of said subject,
  e) means for again determining the amount of an inflammatory marker, preferably osteopontin, GDF-15, and/or CRP, in a sample of said subject; optionally
  f) means for calculating the difference between the values from the first and second measurement; optionally
  g) means for assessing, from the data obtained in steps d), e) and f), if the remodeling is successful; and optionally
  h) means for deciding on adapting the medication depending on the results obtained in steps a) to g).

The term "device" as used herein relates to a system of means comprising at least the aforementioned means operatively linked to each other as to allow the diagnosis. Preferred means for determining the amount of a cardiac troponin and means for determining the amount of a natriuretic peptide, and means for calculating and diagnosing if the subject is suffering from a cardiovascular disorder are disclosed above in connection with the method of the invention. How to link the means in an operating manner will depend on the type of means included into the device. For example, where means for automatically determining the amount of the peptides are applied, the data obtained by said automatically operating means can be processed by, e.g., a computer program in order to obtain the desired results. Preferably, the means are comprised by a single device in such a case. Said device may accordingly include an analyzing unit for the measurement of the amount of the peptides or polypeptides in an applied sample and a computer unit for processing the resulting data for the evaluation. Alternatively, where means such as test stripes are used for determining the amount of the peptides or polypeptides, the means for comparison may comprise control stripes or tables allocating the determined amount to a reference amount. The test stripes are, preferably, coupled to a ligand which specifically binds to the peptides or polypeptides referred to herein. The strip or device, preferably, comprises means for detection of the binding of said peptides or polypeptides to the said ligand. Preferred means for detection are disclosed in connection with embodiments relating to the method of the invention above. In such a case, the means are operatively linked in that the user of the system brings together the result of the determination of the amount and the diagnostic or prognostic value thereof due to the instructions and interpretations given in a manual. The means may appear as separate devices in such an embodiment and are, preferably, packaged together as a kit. The person skilled in the art will realize how to link the means without further ado. Preferred devices are those which can be applied without the particular knowledge of a specialized clinician, e.g., test stripes or electronic devices which merely require loading with a sample. The results may be given as output of raw data which need interpretation by the clinician. Preferably, the output of the device is, however, processed, i.e., evaluated, raw data the interpretation of which does not require a clinician. Further preferred devices comprise the analyzing units/devices (e.g., biosensors, arrays, solid supports coupled to ligands specifically recognizing the natriuretic peptide, Plasmon surface resonance devices, NMR spectrometers, mass-spectrometers etc.) or evaluation units/devices referred to above in accordance with the method of the invention.

Finally, the present invention relates to a kit of diagnosing which medication is to be applied in the remodeling process of a subject after a myocardial infarction, said kit comprising instructions for carrying out the said method and
  a) means for determining the amount of a natriuretic peptide and the amount of a cardiac troponin, in a sample of said subject,
  b) means for determining the amount of an inflammatory marker, preferably osteopontin, GDF-15, CRP, in a sample of said subject; optionally
  c) means for diagnosing if a remodeling in the subject is to be initiated, wherein the medication to be applied in the remodeling is selected according to the level of the peptides determined in a) and b).

Also comprised is a kit of monitoring the remodeling in a subject after a myocardial infarction, wherein the remodeling is supported by medication, said kit comprising instructions for carrying out the said method, means for carrying out steps a), b) and c) as cited beforehand; and
  d) means for again determining the amount of a natriuretic peptide and the amount of a cardiac troponin, in a sample of said subject,
  e) means for determining the amount of an inflammatory marker, preferably osteopontin, GDF-15, CRP, in a sample of said subject; optionally
  f) means for calculating the difference between the values from the first and second measurement; optionally
  g) means for assessing, from the data obtained in d), e) and f), if the remodeling is successful; and optionally
  h) means for deciding on adapting the medication depending on the results obtained in steps a) to g).

The term "kit" as used herein refers to a collection of the aforementioned means, preferably, provided in separately or within a single container. The container, also preferably, comprises instructions for carrying out the method of the present invention. Accordingly, a kit adopted for carrying out the method of the present invention comprises all components required for practicing said method in an ready-to-use manner, e.g., in a premixed form with adjusted concentrations of the components used for determination and/or comparison.

All references cited in this specification are herewith incorporated by reference with respect to their entire disclosure content and the disclosure content specifically mentioned in this specification.

The following Examples shall merely illustrate the invention. They shall not be construed, whatsoever, to limit the scope of the invention.

Example 1

In 202 patients being diagnosed as having acute MI, the parameters NT-proBNP, high sensitive troponin T, CRP, GDF 15 and osteopontin were measured at a timepoint of 2-3 days after infarction and again 3 months after infarction. It was shown that the decline of the parameters depended on the initial level of NT-proBNP. The levels of the peptides individually dropped. A correlation between the parameters could not be determined, meaning they should represent different modes of action.

NT-proBNP levels were determined with an immunoassay on an ELECSYS 2010 with a detection limit of 20 pg/ml.

Figure 2:
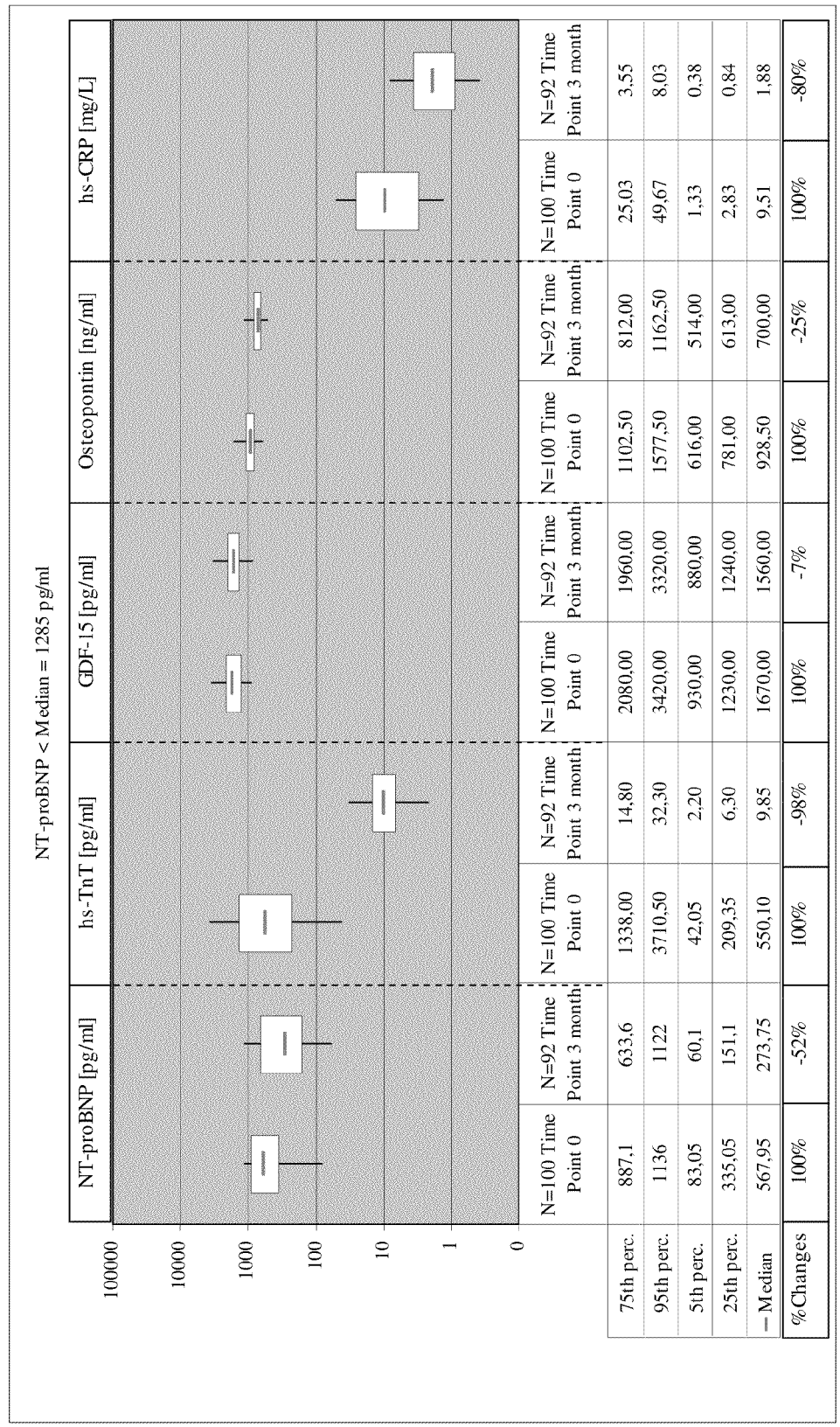
FIG. 2 shows NT-proBNP, hsTNT, GDF-15, ostepontin and hsCRP at time points=0 and =3 month arranged for NT-proBNP below the median of 1285 pg/ml. Values for the median as well as the $5^{th}$, $25^{th}$, $75^{th}$ and $95^{th}$ percentiles as well as the percentage of change are illustrated.
Figure 3:
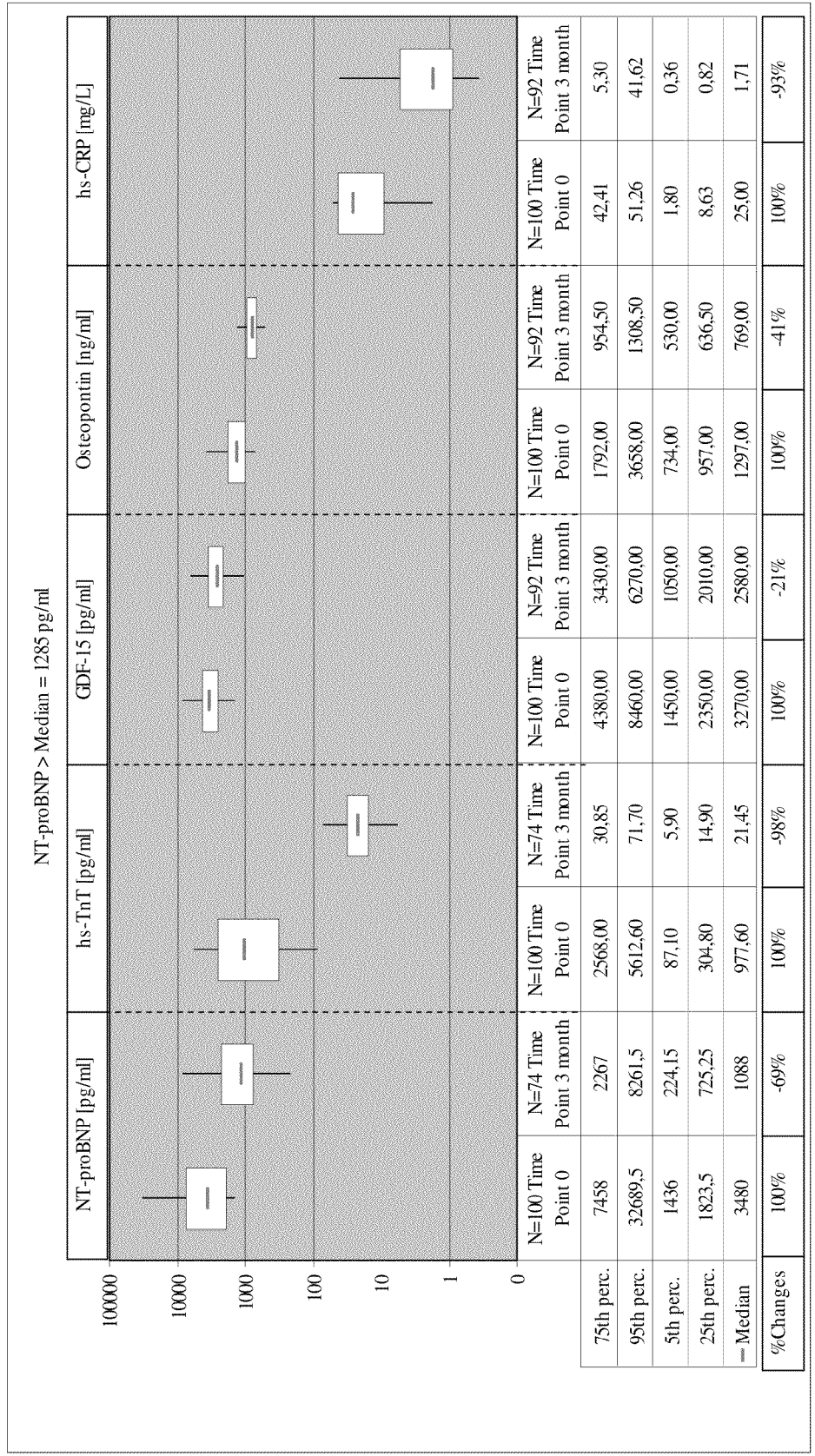
FIG. 3 shows NT-proBNP, hsTNT, GDF-15, ostepontin and hsCRP at time points=0 and =3 month arranged for NT-proBNP above the median of 1285 pg/ml. Values for the median as well as the $5^{th}$, $25^{th}$, $75^{th}$ and $95^{th}$ percentiles as well as the percentage of change are illustrated.
Figure 4:
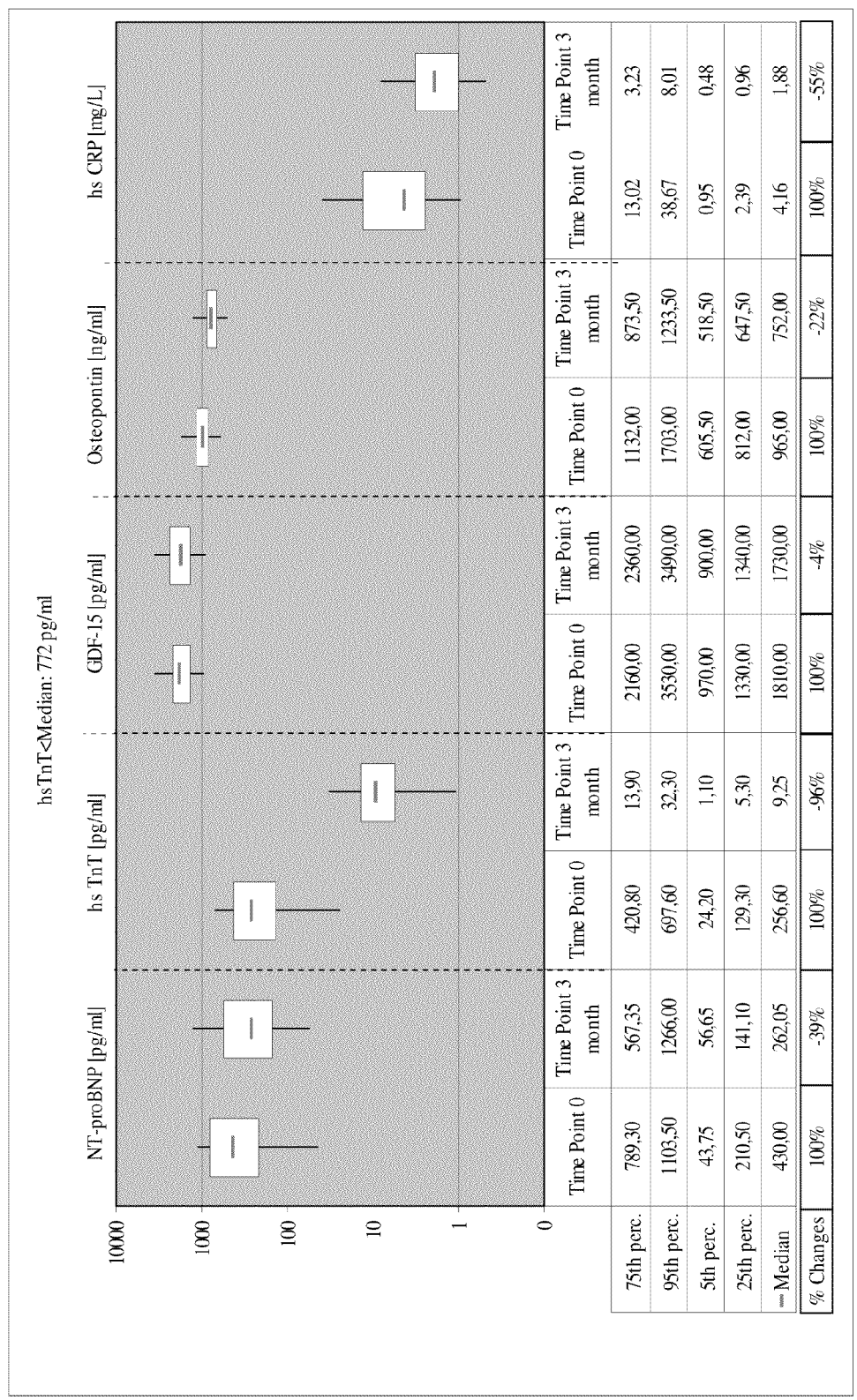
FIG. 4 shows NT-proBNP, hsTNT, GDF-15, ostepontin and hsCRP at time points=0 and =3 month arranged for hsTNT below the median of 772 pg/ml. Values for the median as well as the $5^{th}$, $25^{th}$, $75^{th}$ and $95^{th}$ percentiles as well as the percentage of change are illustrated.
Figure 5:
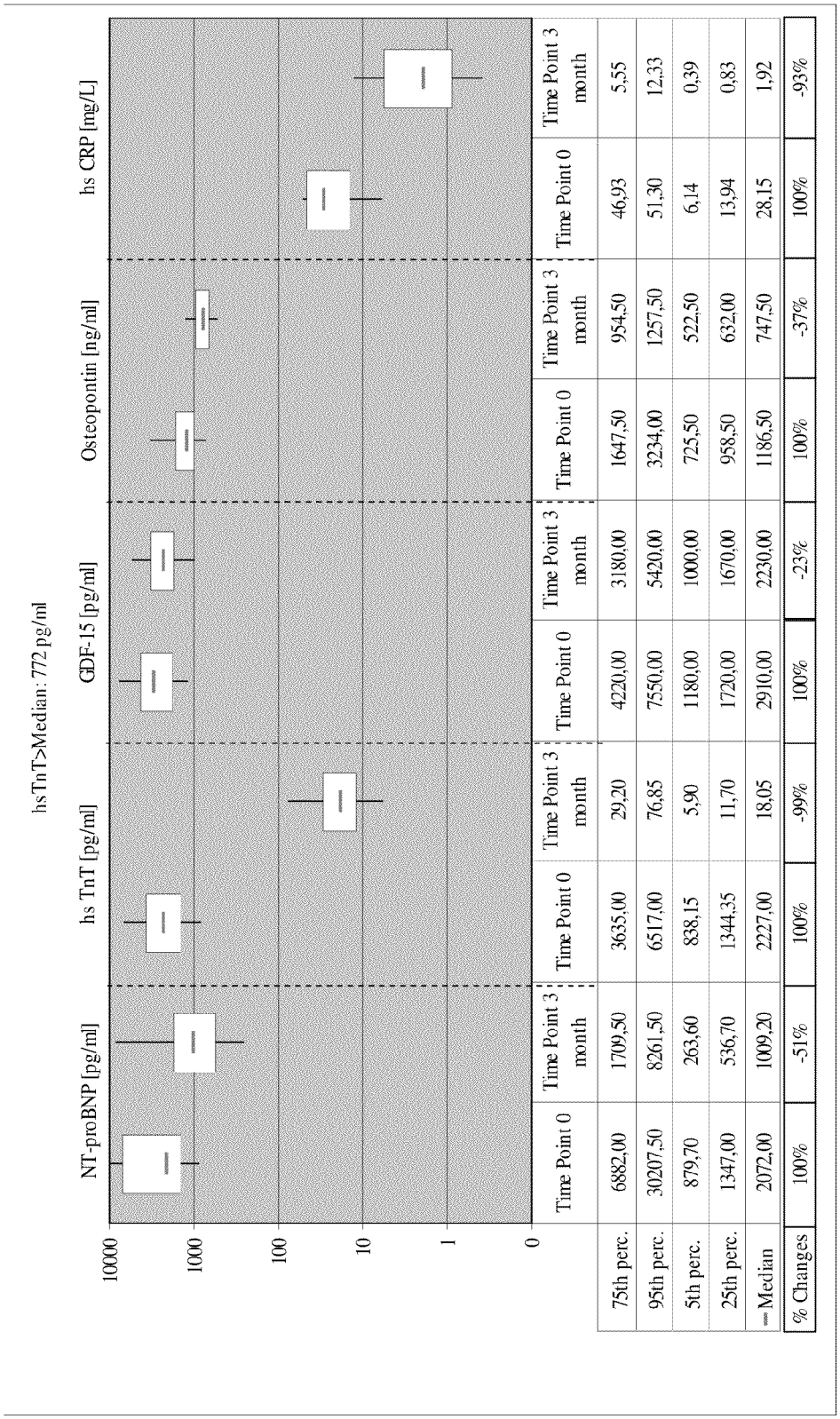
FIG. 5 shows NT-proBNP, hsTNT, GDF-15, ostepontin and hsCRP at time points=0 and =3 month arranged for hsTNT above the median of 772 pg/ml. Values for the median as well as the $5^{th}$, $25^{th}$, $75^{th}$ and $95^{th}$ percentiles as well as the percentage of change are illustrated.
Figure 6:
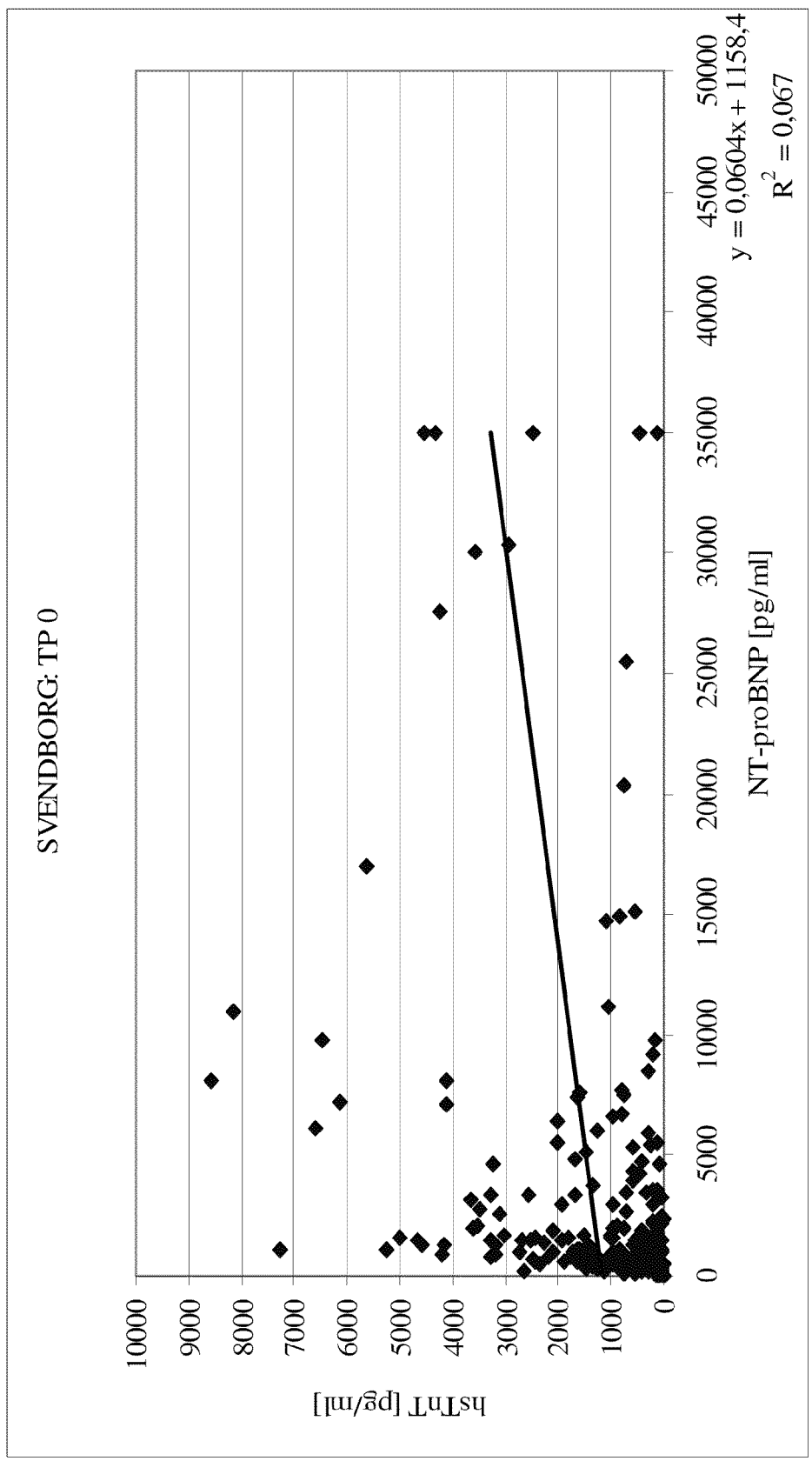
FIG. 6 shows a correlation of the biomarkers hsTNT and NT-proBNP at time point=0 for analyzing whether the biomarkers are dependant or independent.
Figure 7:
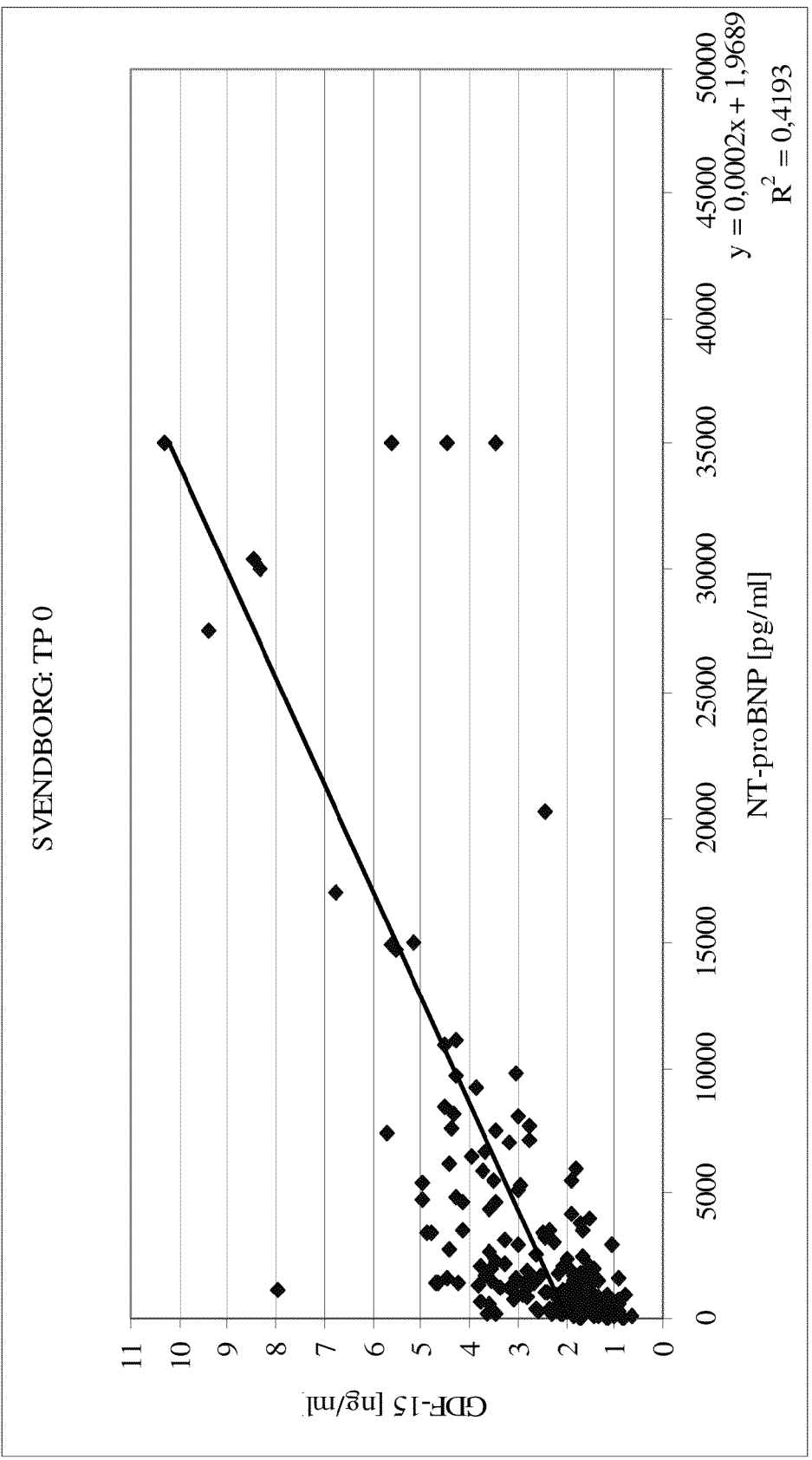
FIG. 7 shows a correlation of the biomarkers GDF-15 and NT-proBNP at time point=0 for analyzing whether the biomarkers are dependant or independent.
Figure 8:
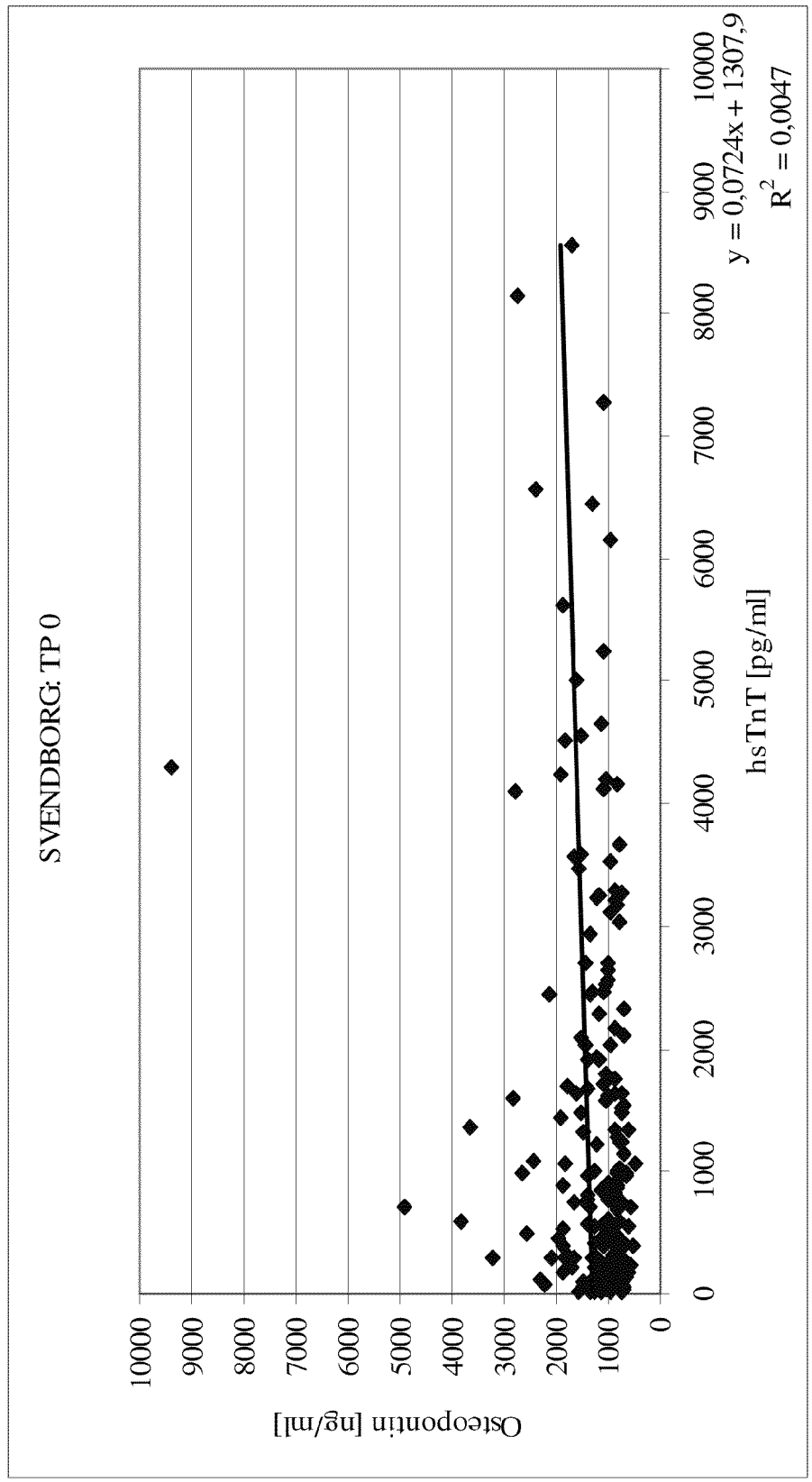
FIG. 8 shows a correlation of the biomarkers osteopontin and hsTNT at time point=0 for analyzing whether the biomarkers are dependant or independent.
Figure 9:
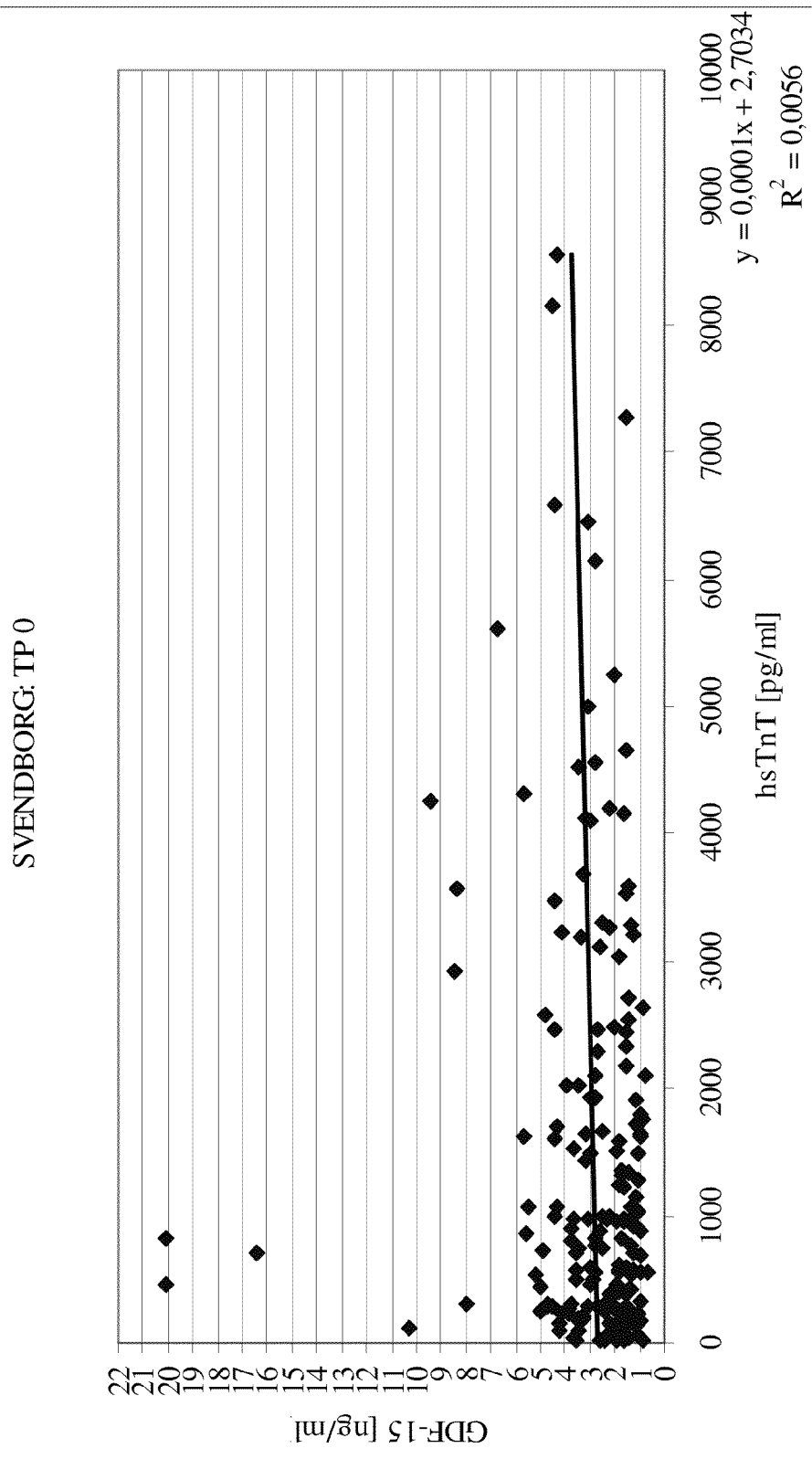
FIG. 9 shows a correlation of the biomarkers GDF-15 and hsTNT at time point=0 for analyzing whether the biomarkers are dependant or independent.
Figure 10:
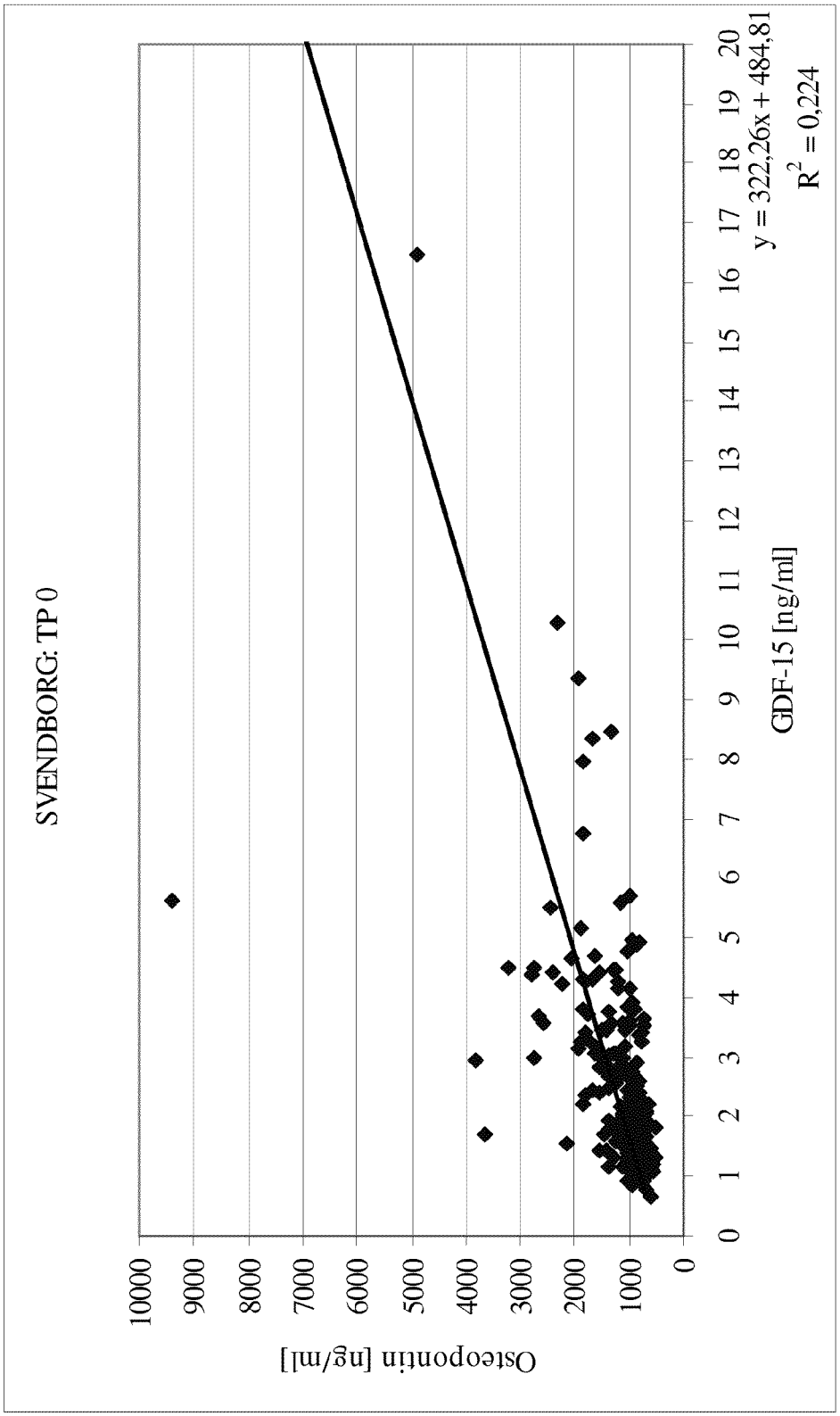
FIG. 10 shows a correlation of the biomarkers osteopontin and GDF-15 at time point=0 for analyzing whether the biomarkers are dependant or independent.

The results of the study are shown in the following table and FIGS. 1 to 10. Herein, FIGS. 1 to 5 illustrate the values cited in the table; they are partly ranged according to the NT-proBNP values above and under the median value and show the change (in %) depending on the initial NT-proBNP value; FIGS. 6 to 10 illustrate the correlations of the initial biomarkers at timepoint=0 and show if these markers are dependent or independent.

|  | NT-proBNP/hsTnT-Ratio Timepoint 0 N = 166 | | | |
| --- | --- | --- | --- | --- |
|  | 41 $1^{st}$ quartile | 41 $2^{nd}$ quartile | 42 $3^{rd}$ quartile | 42 $4^{th}$ quartile |
| Ratio, median (range) | 0.34 (0.10-0.56) | 0.86 (0.56-1.27) | 2.46 (1.32-3.93) | 10.35 (4.10-285.02) |

-continued

| | | | | |
|---|---|---|---|---|
| NT-proBNP [pg/ml], median | 624.10 | 827.2 | 1216.5 | 3369 |
| Hs troponin T [pg/ml], median | 1904.5 | 980.4 | 515.45 | 238.25 |
| GDF-15 [pg/ml], median | 1450 | 1800 | 2280 | 3270 |
| Osteopontin [ng/ml], median | 856 | 1036 | 1050 | 1198.5 |
| Hs CRP [mg/L], median | 16.7 | 13.02 | 15.22 | 9.90 |

| | NT-proBNP/hsTnT-Ratio Timepoint 3 month N = 166 | | | |
|---|---|---|---|---|
| | 41 1. quartile | 41 2. quartile | 42 3. quartile | 42 4. quartile |
| NT-proBNP [pg/ml], median | 273.6 | 481.20 | 759.35 | 1245 |
| Hs troponin T [pg/ml], median | 9.80 | 12.8 | 16.10 | 23.85 |
| GDF-15 [pg/ml], median | 1330 | 1730 | 2410 | 2860 |
| Osteopontin [ng/ml], median | 647 | 728 | 806 | 812 |
| Hs CRP [mg/L], median | 1.55 | 2.11 | 1.92 | 1.81 |

What is claimed is:

1. A method of deciding which treatment is to be administered in a remodeling process of a subject who has suffered a myocardial infarction, the method comprising
   determining an amount of a natriuretic peptide, a cardiac troponin, and an inflammatory marker in a sample from the subject, wherein the inflammatory marker is selected from growth-differentiation factor-15 (GDF-15), C-reactive protein (CRP), and osteopontin, and
   initiating a remodeling process in the subject by administering a treatment selected according to the amounts of natriuretic peptide, cardiac troponin and inflammatory marker determined.

2. The method of claim 1, wherein the natriuretic peptide is selected from the group consisting of atrial natriuretic peptide (ANP), N-terminal pro-atrial natriuretic peptide (NT-proANP), brain natriuretic peptide (BNP) and N-terminal pro-brain natriuretic peptide (NT-proBNP).

3. The method of claim 1, wherein the natriuretic peptide is NT-proBNP.

4. The method of claim 3, wherein treatment comprises administration of a medication selected from the group consisting of beta blockers, natriuretics, loop diuretics, nitrates, and positive inotropic agents if an amount of NT-proBNP ≥300 pg/ml is determined.

5. The method of claim 1, wherein the inflammatory marker is GDF-15.

6. The method of claim 5, wherein treatment comprises administration of a medication selected from the group consisting of ACE inhibitors, angiotensin receptor antagonists, statins, NSAIDS, and selective COX-2 inhibitors if an amount of GDF-15 ≥800 pg/ml is determined.

7. The method of claim 1, wherein the inflammatory marker is C-reactive protein (CRP).

8. The method of claim 7, wherein treatment comprises administering a medication selected from the group consisting of statins if an amount of CRP >3 mg/L is determined.

9. The method of claim 1, wherein the inflammatory marker is osteopontin.

10. The method of claim 9, wherein treatment comprises administering a medication selected from the group consisting of anti-inflammatory drugs, angiotensin receptor antagonists, and aldosterone antagonists if an amount of osteopontin >500 pg/ml is determined.

11. The method of claim 1, wherein the cardiac troponin is troponin T or troponin I.

12. The method of claim 11, wherein the treatment comprises percutaneous intervention further comprising determining a second amount of troponin T between 2-3 days and ten months after determination of the first amount of troponin T, and applying a percutaneous intervention if the second amount does not drop to 80% or less of the first amount.

13. The method according to claim 12, wherein the first amount is determined 2-3 days after infarction and the second amount is determined about 3 months after the first determination.

14. The method according to claim 13, wherein one or more determinations subsequent to the second determination are made at 3-6 month intervals after the second determination.

15. The method of claim 1, wherein the amounts of the natriuretic peptide, cardiac troponin, and inflammatory marker are determined 1 to 3 days following the myocardial infarction.

16. A method of managing treatment of a subject undergoing a remodeling process initiated by administration of medication following a myocardial infarction by monitoring success of the remodeling, the method comprising the steps of:
   determining an amount of a natriuretic peptide, a cardiac troponin, and an inflammatory marker in a sample from the subject, wherein the inflammatory marker is selected from growth-differentiation factor-15 (GDF-15), C-reactive protein (CRP), and osteopontin,
   initiating a remodeling process in the subject by administering a medication selected according to the level of the natriuretic peptide, cardiac troponin, and inflammatory marker determined,
   determining a second amount of the natriuretic peptide, the cardiac troponin, and the inflammatory marker in a sample from the subject,
   calculating a difference between the amounts from the first and second determination of a natriuretic peptide, a difference between the amounts from the first and second determination of cardiac troponin, and a difference between the amounts from the first and second determination of inflammatory marker,
   assessing, from the differences obtained, the success of the remodeling process, and managing the treatment by adapting the administration of medication in accordance with the assessment.

17. The method of claim 16, wherein the inflammatory marker is osteopontin and administration of a medication is lowered if the difference is ≥40%.

18. The method of claim 16 wherein the inflammatory marker is GDF-15 and administration of a medication is lowered if the difference is ≥20%.

19. The method of claim 16, wherein the inflammatory marker is CRP and administration of a medication is lowered if a decrease of said second amount to a level of 33 mg/L CRP occurs.

* * * * *